US00PP29462P2

(12) United States Plant Patent
Ichiba

(10) Patent No.: US PP29,462 P2
(45) Date of Patent: Jul. 3, 2018

(54) ***SCABIOSA* PLANT NAMED 'ICHWHIT'**

(50) Latin Name: ***Scabiosa* hybrid**
Varietal Denomination: ICHWHIT

(71) Applicant: Kaori Ichiba, Tokyo (JP)

(72) Inventor: Kaori Ichiba, Tokyo (JP)

( * ) Notice: Subject to any disclaimer, the term of this patent is extended or adjusted under 35 U.S.C. 154(b) by 0 days.

(21) Appl. No.: 15/530,315

(22) Filed: Dec. 21, 2016

(51) Int. Cl.
*A01H 5/02* (2018.01)

(52) U.S. Cl.
USPC ..... Plt./478

(58) Field of Classification Search
USPC ..... Plt./478
See application file for complete search history.

*Primary Examiner* — Susan McCormick Ewoldt
(74) *Attorney, Agent, or Firm* — Penny J. Aguirre

(57) ABSTRACT

A new cultivar of *Scabiosa*, 'ICHWHIT', that is characterized by its very long blooming period, blooming from May through November in the United Kingdom, Japan and The Netherlands and has shown continuous bloom (12 months and longer) in the Mediterranean climate of Israel, its plant height that reaches 80 cm in height in bloom (foliage height of 40 cm), its inflorescences held on long peduncles, its inflorescences that are very clear white in color with very pale pink coloration in centers as temperatures cool later in the season and its pink anthers that are pronounced and very visible as florets develop.

2 Drawing Sheets

Botanical classification: *Scabiosa* hybrid.
Variety denomination: 'ICHWHIT'.

CROSS REFERENCE TO A RELATED APPLICATION

This application is a U.S. Plant Patent Application filed for a plant derived from the same breeding program that is entitled Scabiosa Plant Named 'ICHPIN' (U.S. Plant Pat. No. 28,303).

BACKGROUND OF THE INVENTION

The present invention relates to a new and distinct cultivar of *Scabiosa* of hybrid origin, botanically known as *Scabiosa* 'ICHWHIT' and will be referred to hereinafter by its cultivar name, 'ICHWHIT'.

The new invention arose from an ongoing controlled breeding program conducted by the Inventor in Tokyo Japan working with collections of the species *Scabiosa columbaria, Scabiosa japonica, Scabiosa incisa* and many hybrids of different species of *Scabiosa*. A key objective of this program was to obtain new cultivars of *Scabiosa* that are healthy with good vigor, very long blooming, have desirable plant heights combined with unique flower colors.

The new cultivar arose from crosses made over a number of years between unnamed and unpatented plants from the Inventor's breeding program and seeds were pooled from the crosses and sown. The exact parentage is unknown. The new cultivar was selected in 2008 as a single unique plant from the above crosses with a reference code of 14SCA-W1.

Asexual propagation of the new cultivar was first accomplished by the Inventor by stem cuttings in 2008 in Tokyo, Japan. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of 'ICHWHIT'.

These characteristics in combination distinguish 'ICHWHIT' as a new and distinct cultivar of *Scabiosa*.

1. 'ICHWHIT' exhibits a very long blooming period, blooming from May through November in the United Kingdom, Japan and The Netherlands and has shown continuous bloom (12 months and longer) in the Mediterranean climate of Israel.
2. 'ICHWHIT' exhibits a plant height that reaches 80 cm in height in bloom (foliage height of 40 cm).
3. 'ICHWHIT' exhibits inflorescences held on long peduncles.
4. 'ICHWHIT' exhibits inflorescences that are very clear white in color with very pale pink coloration in centers as temperatures cool later in the season.
5. 'ICHWHIT' exhibits creamy white and pink anthers that are pronounced and very visible as florets develop.

'ICHWHIT' can be most closely compared to the *Scabiosa* cultivars, 'ICHPIN' and 'Fama White' (seed strain, not patented) 'ICHPIN' is similar to 'ICHWHIT' in having inflorescences that are held on long peduncles and in having a very long blooming period. 'ICHPIN' differs from 'ICHWHIT' in having a shorter plant height, inflorescences that are bright pink in color with white coloration in the centers as temperatures cool later in the season and less visible and less pronounced anthers as florets develop. 'Fama White' is similar to 'ICHWHIT' in having white flowers. 'Fama White' differs from 'ICHWHIT' in having silvery blue foliage and much larger flowers with outer florets that have more ruffled margins and anthers that are white in color.

BRIEF DESCRIPTION OF THE DRAWINGS

The accompanying colored photographs illustrate the overall appearance and distinct characteristics of plants of the new *Scabiosa*.

The photograph in FIG. 1 provides a side view of 'ICHWHIT' 12 months in age as grown in a 2-liter container in a glass greenhouse in Moshav Nehalim, Israel.

Figure 1:
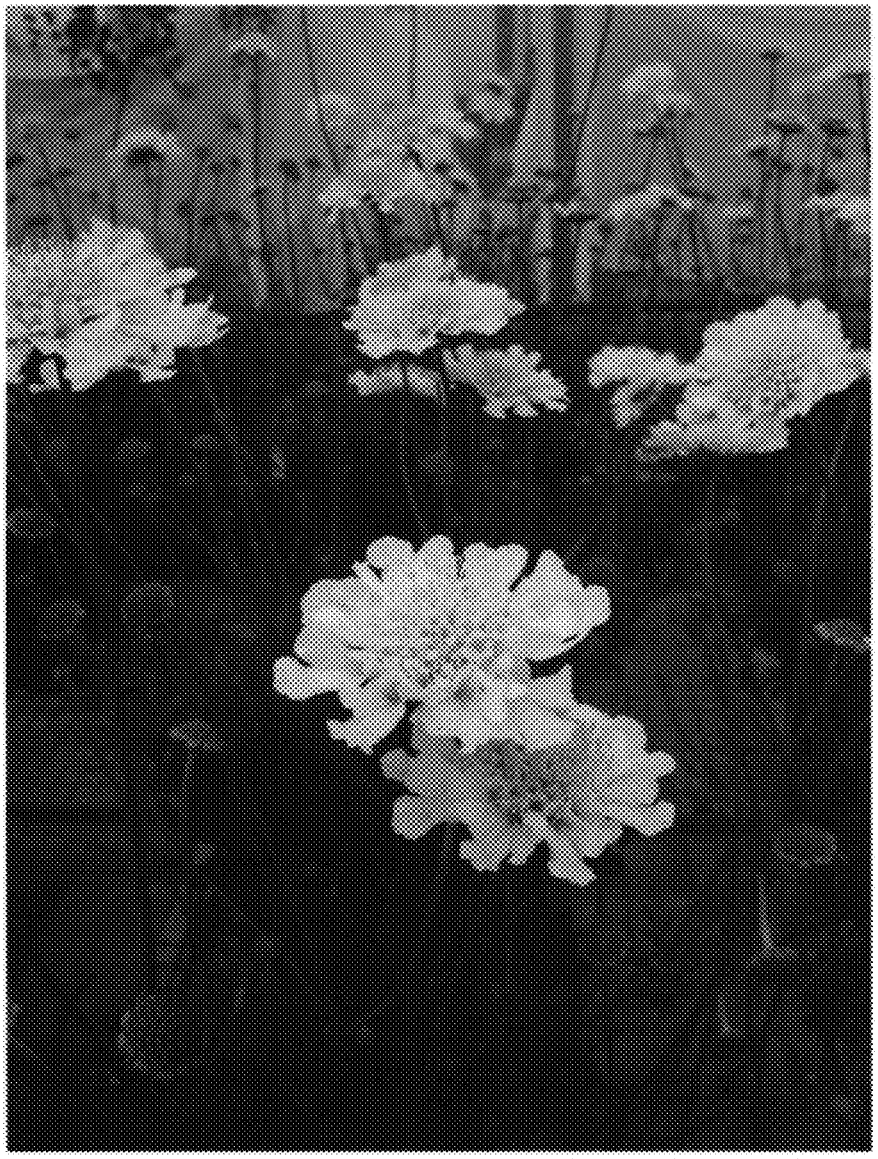
Figure 2:
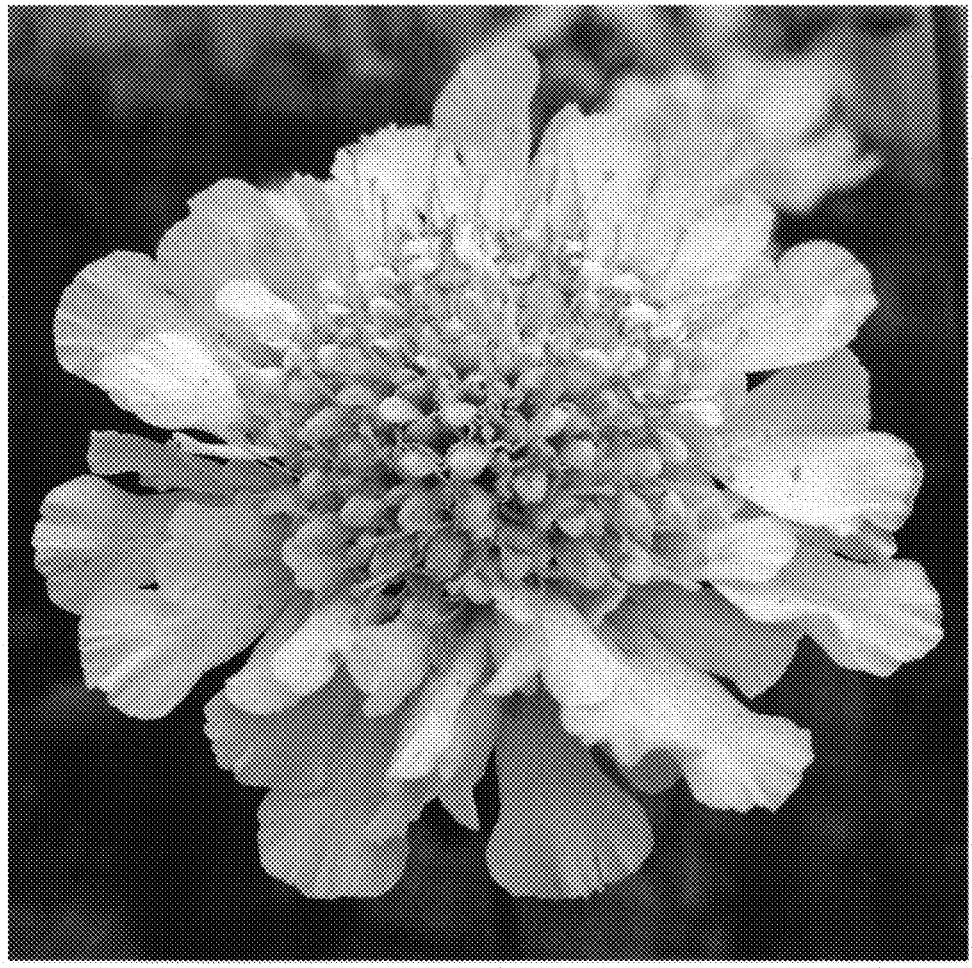

The photograph in FIG. 2 provides a close-up view of the inflorescences of 'ICHWHIT' on a plant 12 months in age as grown outdoors in a 1-liter container in Moshav Nehalim, Israel.

The colors in the photographs may differ slightly from the color values cited in the detailed botanical description, which accurately describes the colors of the new *Scabiosa*.

DETAILED BOTANICAL DESCRIPTION

The following is a detailed description of 12 month-old plants from rooted cuttings of the new cultivar as grown in 5-liter containers in Berkhampstead, Hertfordshire, United Kingdom. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—May through November in the United Kingdom, Japan and Netherlands and has shown continuous bloom 12 months and longer in the Mediterranean climates of Israel.

*Plant habit.*—Herbaceous perennial herb, upright with extended flowering stems.

*Height and spread.*—Reaches an average of 80 cm in height in bloom (foliage height of 40 cm) and 40 cm in width.

*Cold hardiness.*—Cold hardy at least to U.S.D.A Zone 7.

*Disease and pest resistance.*—No susceptibility or resistance to diseases or pests has been observed, plants have been observed to be healthy to date.

*Root description.*—Fine and fibrous.

*Propagation.*—Stem cuttings.

*Root development.*—Roots initiate in 10 to 14 days under greenhouse conditions and rooting cutting plugs will develop to a flowering plant in a 1.5-liter container in 4 months.

*Growth rate.*—Moderate.

Stem description:

*Stem shape.*—Cylindrical.

*Stem color.*—146A.

*Stem size.*—20 to 25 cm in length and 5 to 6 mm in diameter.

*Stem surface.*—Pubescent with un-branched hairs translucent hair.

*Stem strength.*—Strong.

*Branching habit.*—Freely branching with many spreading branches from the base.

Foliage description:

*Leaf division.*—Lower leaves; single, middle leaves; pinnatifid to pinnatisect in upper part of the leaf with 1 to 2 or more pairs of lobes in lower part of the leaf, upper leaves; bipinnatisect.

*Leaf shape.*—Lower leaves; ovate, middle leaves; narrow obovate, upper leaves; ovate.

*Leaf base.*—Lower leaves; decurrent, middle leaves; decurrent, upper leaves; obtuse.

*Leaf apex.*—Lower leaves; obtuse, middle leaves; obtuse, upper leaves; acute.

*Leaf margin.*—Lower leaves; serrate, middle leaves; lobes and leaf divisions have teeth, upper leaves; deeply divided.

*Leaf venation.*—Pinnate, color on upper surface 138D, lower surface 137B.

*Leaf attachment.*—Petiolate on lower leaves, upper and middle leaves appear nearly sessile.

*Leaf arrangement.*—Opposite.

*Leaf surface.*—Pubescent, upper surface; short, straight translucent hairs, lower surface; recurved unbranched translucent hairs.

*Leaf color.*—Upper surface; 137B, lower surface; 137C.

*Leaf size.*—Lower leaves; 7 cm in length (including petiole) and 2 cm in width, middle leaves; 6.5 cm in length (including petiole) and 2 cm in width, upper leaves; Up to 8.5 cm in length and 5 cm in width.

*Leaf number.*—Average of 12 per main branched stem.

*Leaf fragrance.*—None.

*Internode length.*—Up to 6 cm in length.

*Petiole.*—Up to 2.5 mm in length and 2 mm in width, 138C in color, surfaces are covered with un-branched translucent hairs.

Flower description:

*Inflorescence type.*—Flat topped heads of outer and inner florets subtended by leafy, involucral bracts, solitary.

*Lastingness of inflorescence.*—Average of 10 days, self cleaning.

*Inflorescence size.*—4.5 cm to 5.5 cm in diameter, 1.5 cm in depth.

*Inflorescence fragrance.*—None.

*Inflorescence number.*—An average of 1 flowering head on each peduncle comprised of 12 to 18 inner florets and 45 to 50 inner florets.

*Floret form.*—Tubular.

*Floret aspect.*—Outwards to upwards.

*Floret buds.*—Average of 3 mm in depth and diameter, NN155A in color, obovate in shape.

*Corolla.*—Outer florets; asymmetric with narrow tube expanding into 2 lips; an upper lip with 3 large lobes and lower lip with 2 smaller lower lobes (occasionally 3), overall diameter is 1.2 to 1.5 cm, tube; 5 to 7 mm in length and 1 mm in width expanding to 2 mm in width at throat, surfaces are covered with un-branched, NN155A in color, translucent downward pointing hairs, all lobes; surfaces are smooth, margins are rounded and wavy, NN155A in color on both surfaces, upper lip; shape 3 obovate shaped lobes, central lobes 1 to 1.6 cm in length and 1.7 cm in width, lateral lobes 4 to 10 mm in length and 3 to 7 mm in width, lower lip; lobes round in shape, 2 to 3 mm in length and width, inner florets; narrow tube expanding into 2 lips; an upper lip with 3 larger lobes and lower lip with 2 smaller lower lobes, overall diameter is 5 mm, tube; 4 mm in length and 1 mm in width expanding to 2 mm in width at throat, tube surface is minutely hairy, all lobes; surfaces are smooth, margins are wavy, apex rounded, and NN155A in color on both surfaces with a flush of 62D in cool temperatures, upper lip; 3 oblong shaped lobes, central lobes 3 mm in length and 5 mm in width, lateral lobes 2 mm in length and width, lower lip; 2 round shaped lobes, 1 to 1.5 mm in length and 1 to 3 mm in width.

*Involucels.*—Cup-shaped, scarious with a triangular shaped top, outer florets; an average of 1.5 mm in length and 2 mm in width, inner florets; an average of 2 mm in length and 2 mm in width, persistent and enlarging with fruit (encloses ovary), NN155A in color, surfaces are pubescent with a few long hairs.

*Sepals.*—Outer florets; 5, thread like and stiff in shape, an average of 5 mm length, <0.5 mm in width, entire margin, surface minutely hairy, acute apex, truncate base, color is NN155A blending to N186C at the tip, inner florets; 5, thread like and stiff in shape, an average of 4 mm length, <0.5 mm in width, entire margin, surface is minutely hairy, acute apex, truncate base, color is NN155A blending to 77B at the apex.

*Peduncles.*—25 to 35 cm in length and 2.5 mm in diameter (at center), pubescent surface with adpressed, unbranched, translucent hairs, 146A in color fading to 144A towards apex.

*Pedicels.*—None, individual flowers sessile.

*Involucral bracts.*—10 to 12, arrangement is whorl around flower head, linear in shape, 6 to 8 mm in length and 1 mm in width, surfaces are pubescent with short un-branched, adpressed translucent hairs, color; 137A with base 145C, apex acute, base truncate, margins entire, held nearly horizontally.

Reproductive organs:

*Gynoecium.*—Outer florets; pistil; 1, stigma; is capitate shaped, <1 mm in length and width and width and 75A to 75B in color, style; linear in shape, an average of 1.9 mm in length, <0.5 mm in width, NN155A in color, ovary; cylindrical in shape, inferior, 1.5 mm in height and width, surface is minutely pubescent and 145C in color, inner florets; pistil; 1, stigma; is capitate in shape, <1 mm in length and width and 75A to 75B in color, style; linear in shape, an average of 1.4 mm in length and <0.5 mm in width, NN155A in color, ovary; cylindrical in shape, inferior, 1.5 mm in height and 1 mm in width, surface is minutely pubescent and 145C in color.

*Androcoecium.*—Outer florets; stamens; 4, not always exceeding corolla tube, attached to corolla lobes, anthers; color is N74D to 75A (165C when filaments do not extend), 1.5 mm in length and <0.5 mm in width, filaments; an average of 4.5 mm in length and <0.5 mm in width, and NN155D in color, pollen not observed, inner florets; stamens; 4, not always exceeding corolla tube, attached to corolla lobes, anthers; color is N74D to 75A (165C when filaments do not extend), 1.5 mm in length and 0.5 mm in width, filament; is an average of 3.5 mm in length and <0.5 mm in width, and NN155A in color, pollen moderate in quantity and 155A in color on stamens with elongated filaments.

*Fruit/seeds.*—Seed is produced; average of 1 achene per each flower, cylindrical in shape, individual seed size is 3 mm in length and 1.5 mm in width and 1D in color.

It is claimed:

1. A new and distinct cultivar of *Scabiosa* plant named 'ICHWHIT' as herein illustrated and described.

* * * * *